United States Patent
Kim et al.

[11] Patent Number: 5,866,133
[45] Date of Patent: Feb. 2, 1999

[54] **TANNING COSMETICS CONTAINING *CAESAPINIA SAPPAN L.* EXTRACT**

[75] Inventors: Jeong-Ha Kim, Seoul; Beom-Jun Kim; Kang-Tae Lee, both of Chungcheongnam-do; Heong Kwon Jang, Seoul; Jeong Haeng Kim, Keongki-do, all of Rep. of Korea

[73] Assignee: Coreana Cosmetics Co., Limited, Chungcheongnam-do, Rep. of Korea

[21] Appl. No.: 900,883

[22] Filed: Jul. 28, 1997

[30] Foreign Application Priority Data

Jul. 27, 1996 [KR] Rep. of Korea ............... 1996 30755

[51] Int. Cl.[6] .................... A61K 35/78; A61K 7/42; A61K 7/44; A61K 7/00
[52] U.S. Cl. .................... 424/195.1; 424/59; 424/60; 424/400; 424/401
[58] Field of Search .................... 424/59, 60, 400, 424/401, 195.1

[56] References Cited

U.S. PATENT DOCUMENTS 5,352,440 10/1994 Gilchrest et al. .................... 424/59

5,476,651 12/1995 Meybeck et al. .................... 424/59

OTHER PUBLICATIONS

Kurz et al. "Formulating Effective Self–Tanners with DHA" *Cosmetics & Toiletries 109*, 55–61 (1994).

Laden and Zielinski "The Reaction of alpha–Hydroxymethyl Ketones with . . . " *J. Soc. Cos. Chem. 16*, 777–782 (1965).

Alban Muller "Two Tyrosine–Based Suntan Activators" *Cosmetics & Toiletries 107*, 125–132 (1992).

*Primary Examiner*—Shelley A. Dodson
*Attorney, Agent, or Firm*—Heslin & Rothenberg, P.C.; Philip E. Hansen

[57] ABSTRACT

A tanning cosmetic containing *Caesapinia sappan L.* extract is provided. The *Caesapinia sappan L.* extract is prepared by washing the heartwood of *Caesapinia sappan L.* with purified water, drying and crushing into small pieces, extracting with an appropriate solvent and then recovering the extract by evaporating the solvent under reduced pressure. The tanning cosmetic according to the present invention exhibits a continued tanning effect, without causing the problems resulting from UV irradiation.

13 Claims, 1 Drawing Sheet

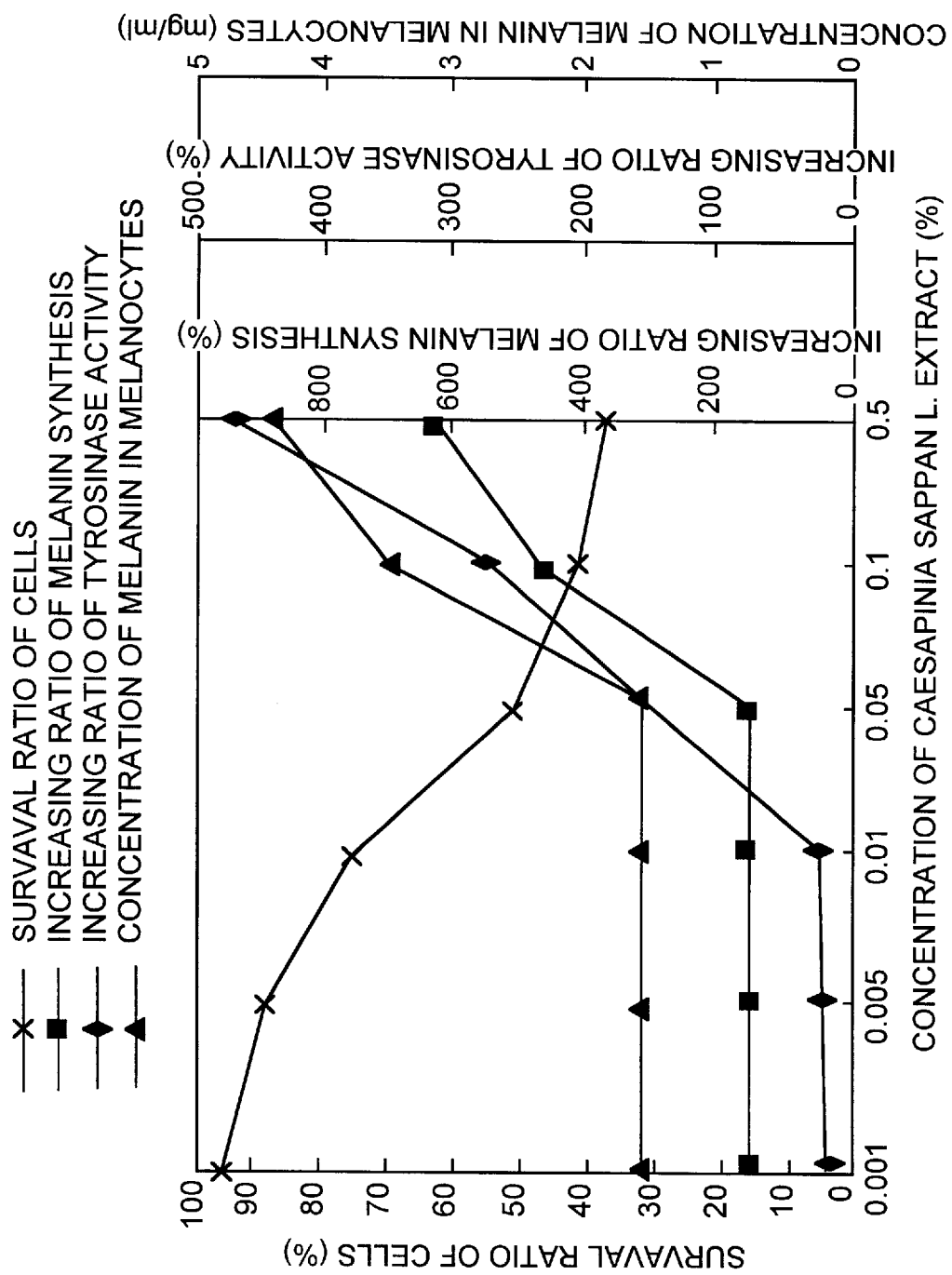

TANNING COSMETICS CONTAINING *CAESAPINIA SAPPAN L.* EXTRACT

FIELD OF THE INVENTION

The present invention relates to cosmetic products having a tanning effect, which contain *Caesapinia sappan L.* extract.

BACKGROUND OF THE INVENTION

In general, natural tanning of skin is to make the skin dark brown. The darkening is caused by distribution of melanin in outer skin cells, which has been synthesized in melanocytes and released therefrom. As the brown skin by tanning looks healthy, young and elegant, many people including Europeans, and even young ladies in Korea recently, love tanned, brown skin.

Up to the present, a usual way for skin tanning was to expose one's body to sunlight naturally, or to artificial ultraviolet (UV) rays irradiated from a UV irradiating device.

However, exposure of skin to UV irradiation for a long time causes side-effects such as wide-aging of skins, that is wrinkles, thickening of outer skin tissue, denaturation of elastin protein and loss of skin elasticity, as well as skin burning, or causes melanoma, the skin cancer. In particular, a strong UV irradiation from sunlight is a matter of great anxiety because of the destruction of the ozone layer.

Thus, other tanning methods having no side-effect of UV irradiation have been studied. One of them is to dye skin by the use of dihydroxy acetone (DHA) (K. Laden et al., J. Soc. Cosmetic Chemist 16, 777–782 (1965); T. Kurz et al., Cosmetics & Toiletries 109, 55–61 (1994)1; or to increase the synthesis of melanin in melanocytes by using tyrosine, tyrosine and hydrolyzed collagen, tyrosine derivatives, or diacyl glycerol WAG) [A. Muller, Cosmetics & Toiletries 107, 125–132 (1992); U.S. Pat. No. 5,352,403.

The earlier method (dyeing with DHA) did not give a natural tanning effect because the dyeing could not be prolonged.

*Caesapinia sappan L.* is a plant belonging to the bean family. The heartwood, excluding the bark and the peripheral part of lignin from the main stalk of *Caesapinia sappan L.*, has been used as a Chinese herb medicine. According to "The Treasures of Eastern Medicine (東醫寶鑑)", *Caesapinia sappan L.* has been used for the promotion of blood circulation, alleviation of pain and treatment of bruises. Among the people, *Caesapinia sappan L.* has been used as a red dye. The coloring components of *Caesapinia sappan L.*, brazilin and hematoxylin, have been used as a hairdye.

SUMMARY OF THE INVENTION

The present inventors have carried out research to develop a tanning method which does not exhibit the problems caused by ultraviolet irradiation and has a continued tanning effect. As a result, they found that *Caesapinia sappan L.* extract promotes the activity of tyrosinase, which is the most important enzyme involved in melanin synthesis in melanocytes, and they have developed a tanning cosmetic comprising *Caesapinia sappan L.* extract, to complete the invention.

The object of the present invention is to provide a safe and effective tanning cosmetic.

In one aspect, the invention relates to a cosmetic composition comprising a pharmaceutically acceptable carrier for topical administration and an amount of *Caesapinia sappan L.* extract sufficient to induce an increase in melanin content in human melanocytes. In one embodiment the composition may contain from 0.01% to 5% by weight of *Caesapinia sappan L.* extract. A preferred composition is in the form of a water-based cream.

In another embodiment, the invention relates to a method of inducing increased skin pigmentation in humans comprising contacting skin with an amount of *Caesapinia sappan L.* extract sufficient to induce an increase in melanin content in human melanocytes.

In another aspect, the invention relates to an extract of *Caesapinia sappan L.* produced by the process of treating *Caesapinia sappan L.* heartwood with a solvent, removing insoluble material and isolating the extract from the solvent. The solvent may be chosen from hydrous and anhydrous $C_1$ to $C_4$ alcohols, $C_1$ to $C_4$ alkyl acetates, acetone and mixtures thereof.

BRIEF DESCRIPTION OF THE DRAWING

FIG. 1. shows the effect of *Caesapinia sappan L.* extract prepared in the Examples on tyrosinase, and on the synthesis of melanin in a melanocyte.

DETAILED DESCRIPTION OF THE INVENTION

The extract used in the present invention is obtained from roots and stems of *Caesapinia sappan L.*, preferably from the heartwood excluding the bark and the peripheral part of lignin from the main stalk of *Caesapinia sappan L.* The extract may be obtained employing the extracting methods described below in more detail.

*Caesapinia sappan L.* is washed with purified water, dried and crushed into small pieces. Thereto is added a one to 10-fold of the dry weight of a lower alkanol such as absolute or hydrous ethanol, methanol, propanol, isopropanol, butanol, or the like, or an organic solvent such as acetone, ethyl acetate, butyl acetate, chloroform, benzene or the like. Then, the mixture is extracted by heating at 40°–90° C. for 3 to 10 hours in an enclosed vessel equipped with a condenser to prevent the evaporation of active components, or at 4°–35° C. for 1–10 days. Then, the extraction solvent is completely evaporated to dryness.

The tanning cosmetic according to the present invention may be formulated as a conventional cream-type cosmetic product.

As the *Caesapinia sappan L.* extract of the present invention promotes the activity of tyrosinase in melanocytes without increasing the number of melanocytes, so that it may increase the biosynthesis of melanin. The extract can increase the content of melanin and tan the skin without using UV irradiation.

The present invention is described in more detail by the examples shown below but is not confined to the scope of the examples.

COMPARATIVE EXAMPLE 1

Heartwood of *Caesapinia sappan L*, (1 kg), which had been washed with purified water and dried, was added to water (5 L) and extracted by heating in an extractor equipped with a condenser for 5 hours. After extracting, it was filtered through a 300 mesh filter. After standing at 5°–10° C. for 7 to 10 days for aging of the crude extract, the resultant material was filtered through Whatman No. 5 filter paper. The filtrate was concentrated to dryness by using rotary evaporator at 80° C. to give the extract (dry weight: 21.61 g).

COMPARATIVE EXAMPLE 2

Heartwood of *Caesapinia sappan L.* (1 kg), which had been washed with purified water and dried, was added to water (5 L) and extracted at 15°–35° C. for 5 days. The crude extract was filtered through 300 mesh filter and again filtered through Whatman No. 2 filter paper. The filtrate was concentrated to 2 times concentration by using a rotary evaporator. Thereto was added 100% ethanol(2.5 L) and stood at 4°–10° C. for 7–10 days for aging. The resultant material was filtered through Whatman No. 2 filter paper. The filtrate was concentrated to dryness by using rotary evaporator at 60° C. to give the extract (dry weight: 13.10 g).

EXAMPLE 1

Heartwood of *Caesapinia sappan L.* (1 kg), which had been washed with purified water and dried, was added to 10% ethanol (5 L) and extracted by heating in an extractor equipped with a condenser for 5 hours, and the crude extract was filtered through a 300 mesh filter. After standing at 5°–10° C. for 7 to 10 days for aging of the crude extract, the resultant material was filtered through Whatman No. 5 filter paper. The filtrate was concentrated to dryness by using rotary evaporator at 60° C., to give the extract (dry weight: 21.61 g).

EXAMPLE 2

The procedure of Example 1 was repeated but using 20% ethanol as a solvent for extraction, to give the extract (dry weight: 38.87 g).

EXAMPLE 3

The procedure of Example 1 was repeated but using 30% ethanol as a solvent for extraction, to give the extract (dry weight: 45.52 g).

EXAMPLE 4

The procedure of Example 1 was repeated but using 40% ethanol as a solvent for extraction, to give the extract (dry weight: 50.12 g).

EXAMPLE 5

The procedure of Example 1 was repeated but using 50% ethanol as a solvent for extraction, to give the extract (dry weight: 53.65 g).

EXAMPLE 6

The procedure of Example 1 was repeated but using 60% ethanol as a solvent for extraction, to give the extract (dry weight: 61.71 g)

EXAMPLE 7

The procedure of Example 1 was repeated but using 70% ethanol as a solvent for extraction, to give the extract (dry weight: 68.69 g).

EXAMPLE 8

The procedure of Example 1 was repeated but using 80% ethanol as a solvent for extraction, to give the extract (dry weight: 80.01 g).

EXAMPLE 9

The procedure of Example I was repeated but using 90% ethanol as a solvent for extraction, to give the extract (dry weight: 84.67 g).

EXAMPLE 10

The procedure of Example 1 was repeated but using 100% ethanol as a solvent for extraction, to give the extract (dry weight: 105.11 g).

EXAMPLE 11

Heartwood of *Caesapinia sappan L.* (1 kg), which had been washed with purified water and dried, was added to 10% ethanol (5 L) and extracted at 15°–35° C. for 5 days. After filtering through a 300 mesh filter and standing at 5°–10° C. for 7 to 10 days for aging of the extract, the resultant material was filtered through Whatman No. 5 filter paper. The filtrate was concentrated to dryness by using rotary evaporator at 60° C. to give the extract (dry weight: 15.27 g).

EXAMPLE 12

The procedure of Example 11 was repeated but using 20% ethanol, as a solvent for extraction, to give the extract (dry weight: 19.85 g).

EXAMPLE 13

The procedure of Example 11 was repeated but using 30% ethanol as a solvent for extraction, to give the extract (dry weight: 24.53 g).

EXAMPLE 14

The procedure of Example 11 was repeated but using 40% ethanol as a solvent for extraction, to give the extract (dry weight: 28.71 g).

EXAMPLE 15

The procedure of Example 11 was repeated but using 50% ethanol as a solvent for extraction, to give the extract (dry weight: 34.63 g).

EXAMPLE 16

The procedure of Example 11 was repeated but using 60% ethanol as a solvent for extraction, to give the extract (dry weight: 39.25 g).

EXAMPLE 17

The procedure of Example 11 was repeated but using 70% ethanol as a solvent for extraction, to give the extract (dry weight: 43.72 g).

EXAMPLE 18

The procedure of Example 11 was repeated but using 80% ethanol: as a solvent for extraction, to give the extract (dry weight: 49.37 g).

EXAMPLE 19

The procedure of Example 11 was repeated but using 90% ethanol as a solvent for extraction, to give the extract (dry weight: 55.69 g).

EXAMPLE 20

The procedure of Example 11 was repeated but using 100% ethanol as a solvent for extraction, to give the extract (dry weight: 68.54 g).

EXAMPLE 21

The procedure of Example 11 was repeated but using methanol as a solvent for extraction, to give the extract (dry weight: 109.48 g).

EXAMPLE 22

The procedure of Example 11 was repeated but using n-propanol as a solvent for extraction, to give the extract (dry weight: 24.39 g).

EXAMPLE 23

The procedure of Example 11 was repeated but using isopropanol as a solvent for extraction, to give the extract (dry weight. 24.78 g).

EXAMPLE 24

The procedure of Example 11 was repeated but using 2-butanol as a solvent for extraction, to give the extract (dry weight: 39.02 g).

EXAMPLE 25

The procedure of Example 11 was repeated but using acetone as a solvent for extraction, to give the extract (dry weight: 15.58 g).

EXAMPLE 26

The procedure of Example 11 was repeated but using chloroform as a solvent for extraction, to give the extract (dry weight: 7.86 g).

EXAMPLE 27

The procedure of Example 11 was repeated but using ethyl acetate as a solvent for extraction, to give the extract (dry weight: 25.88 g).

EXAMPLE 28

The procedure of Example 11 was repeated but using butyl acetate as a solvent for extraction, to give the extract (dry weight: 14.61 g).

EXPERIMENTAL EXAMPLE 1

Effect of *Caesapinia sappan L.* Extract on Tyrosinase activity.

The effect of each of the *Caesapinia sappan L.* extracts obtained from Comparative examples 1 and 2 and from Examples 1–28 on tyrosinase activity was measured.

A tyrosinase, commercially available from SIGMA, which had been isolated from mushroom and purified, was used. The substrate, tyrosine was used as a solution (0.3 mg/ml) dissolved in 0.05M sodium phosphate buffer (pH 6.8).

Each extract obtained from Comparative examples 1 and 2 and Examples 1–28 was dissolved in propylene glycol at a high concentration, and the solution was further diluted to an appropriate concentration with the buffer solution, to give an extract sample.

Tyrosine solution (0.5 ml) was placed in a test tube and the extract sample (0.5 ml) was added thereto. The test tube was stood in an incubator at 37° C. for 10 minutes, and then 210 Unit/ml tyrosinase (0.5 ml) was added thereto. The reaction was carried out at the same temperature for 10 minutes. As a control group, only buffer solution (0.5 ml) was added instead of each extract. The reaction was quenched by placing the test tube on ice to inhibit further reaction in the system. Absorbance was measured at a wavelength of 475 nm by using a spectrophotometer.

The effect of each extract on tyrosinase activity was determined by the formula below:

Increasing ratio of tyrosinase activity(%)=(100×Absorbance of each extract/Absorbance of control group)−100

The results are shown in Table 1.

TABLE 1

Effect of *Caesapinia sappan* L- extracts on Tyrosinase activity

| Experimental material | Final experimental concentration (% W/V) | Increasing ratio of tyrosinase activity (%) |
|---|---|---|
| Comparative example 1 | 0.05 | 14.87 |
| Comparative example 2 | 0.05 | — |
| Example 1 | 0.05 | 24.18 |
| Example 2 | 0.05 | 87.54 |
| Example 3 | 0.05 | 99.56 |
| Example 4 | 0.05 | 122.88 |
| Example 5 | 0.05 | 125.67 |
| Example 6 | 0.05 | 148.09 |
| Example 7 | 0.05 | 171.88 |
| Example 8 | 0.05 | 184.20 |
| Example 9 | 0.05 | 200.17 |
| Example 10 | 0.05 | 211.88 |
| Example 11 | 0.05 | 36.81 |
| Example 12 | 0.05 | 119.43 |
| Example 13 | 0.05 | 161.97 |
| Example 14 | 0.05 | 208.52 |
| Example 15 | 0.05 | 268.69 |
| Example 16 | 0.05 | 312.55 |
| Example 17 | 0.05 | 394.54 |
| Example 18 | 0.05 | 438.86 |
| Example 19 | 0.05 | 435.24 |
| Example 20 | 0.05 | 426.81 |
| Example 21 | 0.05 | 429.86 |
| Example 22 | 0.05 | 325.81 |
| Example 23 | 0.05 | 292.50 |
| Example 24 | 0.05 | 311.62 |
| Example 25 | 0.05 | 216.88 |
| Example 26 | 0.05 | 15.33 |
| Example 27 | 0.05 | 244.93 |
| Example 28 | 0.05 | 231.04 |

EXPERIMENTAL EXAMPLE 2

Effect of *Caesapinia sappan L.* Extract on tyrosinase activity depending upon the concentration of the extract The effect of *Caesapinia sappan L.* extract prepared in Example 18 on tyrosinase activity was examined according to the same procedures as Experimental Example 1. The final concentration of tyrosinase was 100 unit/ml.

The experimental results are shown in Table 2 below.

TABLE 2

Tyrosinase activity dependina upon the concentration of *Caesapinia sappan* L. extract

| Final concentration of *Caesapinia sappan* L. extract (mg/ml) | Increasing ratio of tyrosinase activity (%) |
|---|---|
| 0.01 | 15.12 |
| 0.05 | 18.12 |
| 0.10 | 45.41 |
| 0.20 | 135.86 |
| 0.40 | 381.76 |
| 0.60 | 445.29 |
| 0.80 | 608.87 |
| 1.00 | 336.41 |

Where the concentration of *Caesapinia sappan L.* was not more than 0.8 mg/ml, tyrosinase activity was increased. Thus, in these cases, *Caesapinia sappan L.* extract worked as an enzyme activator for tyrosinase. On the other hand, where the concentration of *Caesapinia sappan L.* extract was more than 0.8 mg/ml, the extract rather inhibited the activity of tyrosinase.

EXPERIMENTAL EXAMPLE 3
Effect of *Caesapinia sappan L.* Extract on multiplication of melanocytes Melanocytes commercially available B16-F1 melanoma (ATCC CRL6323) cell line derived from mouse were used.

The melanoma cell line was inoculated in DMEM culture medium containing glucose (4–5 g/L), 10% blood serum and 1% antibiotic agent, and cultured at 37° C. in a 25 cm$^2$ T flask. After culturing in a condition of 5% $CO_2$ for 24 hours, the cultured medium was treated with 0.05% trypsin containing 0.02% EDTA to separate the cells. Cells (4000 cells per 0.1 ml) were inoculated in a 96-well plate and cultured at 37° C. for 24 hours. After culturing, a proper concentration of *Caesapinia sappan L* extract diluted in DMEM culture medium was added to each of the 96 wells in an amount of 10 µl per well. After further 24 hours culturing, a solution of MTT (5 mg/ml) in saline phosphate buffer solution (PBS) was added to the 96-well plate in an amount of 10 µl per a well. Then the mixture was reacted at 37° C. for 4 hours. After completely isolating the materials in the 96-well plate, acid-treated isopropanol (0.1N HCl) containing 10% Triton X-100 (MTT-dissolved solution) was added (100 µl per well) and the mixture stirred for 20 minutes. The absorbances at 570 and 630 nm were measured by using ELISA measured instrument.

As shown in Table 3 below, the experimental results demonstrated that *Caesapinia sappan L.* extract has no effect on the multiplication of melanocytes.

TABLE 3

Effect of *Caesapinia sappan* L. extract on multiplication of melanocytes

| Final concentration of *Caesapinia sappan* L. (%, w/v) | Survival ratio of melanocytes (%) |
| --- | --- |
| 0.001 | 92.71 |
| 0.005 | 89.06 |
| 0.01 | 74.41 |
| 0.05 | 51.58 |
| 0.1 | 49.65 |
| 0.5 | 47.65 |

EXPERIMENTAL EXAMPLE 4
Effect of *Caesapinia sappan L.* extract on melanin synthesis in melanocytes Melanocytes were cultured by a method identical to Experimental Example 3.

The melanoma cell line (4×10$^4$ cells/well) was inoculated in a 6-well plate, and cultured at 37° C. for 24 hours. The cultured melanoma cells were treated with a proper concentration of *Caesapinia sappan L.* extract diluted in DMEM culture medium, and the mixture cultured at 37° for 24 hours.

After completely removing the culture medium, the cells were separated by treatment with 1 ml of saline-phosphate buffer solution (PBS) containing 0.02% EDTA and 0.05% trypsin. Then, the material was centrifuged at 1,000 rpm for 5 minutes to obtain only cells. The cells were treated with 5% trichloroacetate (TCA), stirred and centrifuged, and the precipitated melanin was washed with saline-phosphate buffer solution. The melanin was treated with 1N NaOH to be dissolved therein, and absorbance of the solution at 475 nm was measured. The melanin concentration was determined by a standard concentration curve of synthesized melanin.

The results are shown in Table 4 below.

TABLE 4

Change of melanin content in melanocytes due to *Caesapinia sappan* L. extract

| Final concentration of *Caesapinia sappan* L. Extract (%, w/v) | Increasing ratio of melanin content (%) |
| --- | --- |
| 0.001 | 157.9 |
| 0.005 | 157.9 |
| 0.01 | 157.9 |
| 0.05 | 157.9 |
| 0.1 | 473.9 |
| 0.5 | 631.8 |

As the concentration of *Caesapinia sappan L.* extract increased, the melanin content in melanocytes also increased. Combining the results of Experimental Examples 1 to 4 (FIG. 1), it is understood that, as the concentration of *Caesapinia sappan L.* extract increases, tyrosinase activity in melanocytes increases, without multiplication of melanocytes, to promote the synthesis of melanin.

FORMULATION I

An exemplary formulation of a cream-type cosmetic containing *Caesapinia sappan L.* extract is described below. The *Caesapinia sappan L.* extract prepared in Example 18 is used.

|  | Parts per weight |
| --- | --- |
| *Caesapinia sappan* L. extract | 0.1 |
| Polyacrylamide, $C_{13-14}$ Isoparaffin and Laureth T | 2.5 |
| Caprylic/capric triglyceride | 3.0 |
| Distilled water | 84.0 |
| Propylene glycol | 10.0 |
| Preservative (s) | 0.4 |

What is claimed is:

1. A cosmetic composition comprising a pharmaceutically acceptable carrier for topical administration and an amount of *Caesapinia sappan L.* extract sufficient to induce an increase in melanin content in human melanocytes.

2. A cosmetic composition according to claim 1 wherein said amount of *Caesapinia sappan L.* extract is from 0.01 to 5% by weight.

3. A cosmetic composition according to claim 1 in the form of a water-based cream.

4. A cosmetic composition comprising a pharmaceutically acceptable carrier for topical administration and an extract from *Caesapinia sappan L.*, said extract obtained by treating *Caesapinia sappan L.* with a solvent, removing insoluble material and isolating said extract from said solvent.

5. A cosmetic composition according to claim 4 wherein said solvent is chosen from hydrous and anhydrous $C_1$ to $C_4$ alcohols and mixtures thereof.

6. A cosmetic composition according to claim 4 wherein said solvent is chosen from acetone, ethyl acetate, butyl acetate, chloroform and benzene.

7. A cosmetic composition according to claim 4 wherein said treating with a solvent is carried out at 40° to 90° C. for 3 to 10 hours.

8. A cosmetic composition according to claim 4 wherein said treating with a solvent is carried out at 4° to 35° C. for 1 to 10 days.

9. A cosmetic composition according to claim 4 wherein said extract from *Caesapinia sappan L.* is obtained from heartwood of *Caesapinia sappan L.*

10. A method of inducing increased skin pigmentation in humans comprising contacting skin with an amount of *Caesapinia sappan L.* extract sufficient to induce an increase in melanin content in human melanocytes.

11. A method according to claim 10 wherein said skin is contacted with a water-based cream containing from 0.01 to 5% by weight of *Caesapinia sappan L.* extract.

12. A method according to claim 10 wherein said extract from *Caesapinia sappan L.* is obtained by treating *Caesapinia sappan L.* heartwood with a solvent, removing insoluble material and isolating said extract from said solvent.

13. A method according to claim 12 wherein said solvent is chosen from hydrous and anhydrous $C_1$ to $C_4$ alcohols, $C_1$ to $C_4$ alkyl acetates, acetone, and mixtures thereof.

* * * * *